United States Patent
Checinski

(10) Patent No.: US 12,202,789 B2
(45) Date of Patent: Jan. 21, 2025

(54) PROCESS FOR THE CONTINUOUS PRODUCTION OF METHANOL

(71) Applicant: CreativeQuantum GmbH, Berlin (DE)

(72) Inventor: Marek Pawel Checinski, Berlin (DE)

(73) Assignee: CREATIVEQUANTUM GMBH, Berlin (DE)

( * ) Notice: Subject to any disclaimer, the term of this patent is extended or adjusted under 35 U.S.C. 154(b) by 0 days.

(21) Appl. No.: 18/560,685

(22) PCT Filed: Dec. 22, 2022

(86) PCT No.: PCT/EP2022/087513
§ 371 (c)(1),
(2) Date: Nov. 14, 2023

(87) PCT Pub. No.: WO2023/126310
PCT Pub. Date: Jul. 6, 2023

(65) Prior Publication Data
US 2024/0270668 A1    Aug. 15, 2024

(30) Foreign Application Priority Data
Dec. 28, 2021 (DE) ...................... 10 2021 006 375.9

(51) Int. Cl.
C07C 31/04 (2006.01)
C07C 29/152 (2006.01)
C07C 29/153 (2006.01)

(52) U.S. Cl.
CPC ............ *C07C 31/04* (2013.01); *C07C 29/152* (2013.01); *C07C 29/153* (2013.01)

(58) Field of Classification Search
CPC ...... C07C 31/04; C07C 29/152; C07C 29/153
See application file for complete search history.

(56) References Cited

U.S. PATENT DOCUMENTS

2003/0158270 A1    8/2003  Mahajan
2011/0144391 A1*   6/2011  Becker ................... B01J 8/1827
                                                  422/600

FOREIGN PATENT DOCUMENTS

WO    WO 2020/136003 A1    7/2020

OTHER PUBLICATIONS

Bakopoulos, multiphase fluidization in large scale slurry jet loop bubble columns for methanol and or dimethyl production, (Chemical Engineering Science 61 (2006) 538-557).*

Henkel, Klaus-Dieter; "Reactor Types and Their Industrial Applications"; *Ullmann's Encyclopedia of Industrial Chemistry—Principles of Chemical Reaction Engineering and Plant Design*; Jan. 1, 1992; pp. 87-120; vol. B4; XP002072387; Wiley-VCH Verlag Gmbh & Co. KG; Weinheim, Germany.

* cited by examiner

*Primary Examiner* — Jafar F Parsa
(74) *Attorney, Agent, or Firm* — LEYDIG, VOIT & MAYER, LTD.

(57) ABSTRACT

A process for the production of methanol from hydrogen and carbon monoxide includes contacting the hydrogen and carbon monoxide with a liquid in at least one bubble or loop or jet loop reactor. The liquid comprises at least one solvent, an alcohol and/or an amine as a nucleophilic promoter, optionally an additional base and a catalyst, the catalyst comprising a transition metal and at least one Lewis base ligand. At least one device is provided for heat removal from the reactor. Methanol is formed as a product.

17 Claims, 5 Drawing Sheets

PROCESS FOR THE CONTINUOUS PRODUCTION OF METHANOL

CROSS REFERENCE TO RELATED APPLICATIONS

This application is a U.S. National Phase application under 35 U.S.C. § 371 of International Application No. PCT/EP2022/087513, filed on Dec. 22, 2022, and claims benefit to German Patent Application No. DE 10 2021 006 375.9, filed on Dec. 28, 2021. The International Application was published in English on Jul. 6, 2023 as WO 2023/126310 A1 under PCT Article 21(2).

FIELD

The invention relates to a process for the production of methanol from hydrogen and carbon monoxide, both of which are present in gaseous form. In particular, the invention relates to the use of a suitable reactor and to the separation of the process product.

BACKGROUND

Methanol, also known as methyl alcohol, is an organic chemical compound with the molecular formula $CH_3OH$. Methanol is one of the most widely produced organic chemicals, with current annual production of almost 100 million tonnes, and this is because methanol is an important starting material, especially for the basic products of aldehyde, formic acid and acetic acid. In addition, methanol and its derivatives are used as an energy source, in particular methane can be formed from it. In addition, methanol is needed for the synthesis for biodiesel and the anti-knock agent MTBE. Methanol can also play a role in the seasonal storage of electrical energy. For example, this is through direct (direct methanol fuel cells) or indirect ($H_2$ reformers) reconversion to electricity using fuel cells, or combustion in appropriately adapted turbines. Lastly, methanol has a high volumetric and gravimetric energy density and therefore is particularly important for the future for all those decentralised fluctuating energy generation processes that are dependent on meteorological conditions, namely solar and wind power, as methanol can be easily transported. Description of the problem and previous fundamental technical implementation:

Currently, industrial methanol production is mainly heterogeneously catalysed with the gaseous reactants carbon monoxide (CO) and hydrogen ($H_2$) on solid catalysts, mostly copper-zinc-aluminium-based oxides. The main disadvantages of this heterogeneous catalysis of methanol from synthesis gas are the high temperatures and pressures used. The conversion of carbon monoxide and hydrogen to methanol has a standard enthalpy of −90.6 kJ/mol, which means that the higher the temperature, the more the equilibrium shifts towards the starting compounds carbon monoxide and hydrogen. Since the heterogeneous catalysts require high activation energies and thus high temperatures, this reduces the proportion of product in the reaction equilibrium. This in turn leads to the need for high pressures to shift the equilibrium to the product side. Despite these measures, the typical yield per reactor cycle is only about 6-15 wt. % and unreacted CO and $H_2$ must be circulated at great expense. The compression of the reactants and the recompression of the non-consumed gases leads to a high energy demand for this type of production process, which results in high OPEX shares of the methanol production price. Since this type of conversion requires a high temperature, in addition to the high exotherm of the reaction itself, intensive cooling of the reactor and especially the catalyst is necessary. Due to the nature of this approach with gaseous reactants and solid catalysts, a relevant proportion of the heat is released at the catalyst, the optimal performance of which is also only guaranteed in a low temperature window.

The industrial production processes to date are linked to the fundamental properties of copper-zinc-aluminium-oxide catalysis, and the plant components, as well as the efficient coupling of material and energy flows, are linked to this fundamental property of the catalyst. However, the economic efficiency of the industrial process is always significantly influenced by two factors: the thermodynamics of the equilibrium ($CO+2H_2 \leftrightarrow CH_3OH$) based on the reactants and products, and the activation barrier based on the catalytic approach. Although the so-called low-pressure process with heterogeneous catalysts can be realised on a large scale today with equally good yields, temperatures >200° ° C. and a pressure of 50 to 100 bar still prevail in this process. This high load on the plant components also leads to considerable investment costs and increases the CAPEX share of the methanol production price.

SUMMARY

In an embodiment, the present disclosure provides a process for the production of methanol from hydrogen and carbon monoxide. The process includes contacting the hydrogen and carbon monoxide, which are both in gaseous form, with a liquid in at least one bubble or loop or jet loop reactor. The liquid comprises at least one solvent, an alcohol and/or an amine as a nucleophilic promoter, optionally an additional base and a catalyst, the catalyst comprising a transition metal and at least one Lewis base ligand. At least one device is provided for heat removal from the reactor. Methanol is formed as a product

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
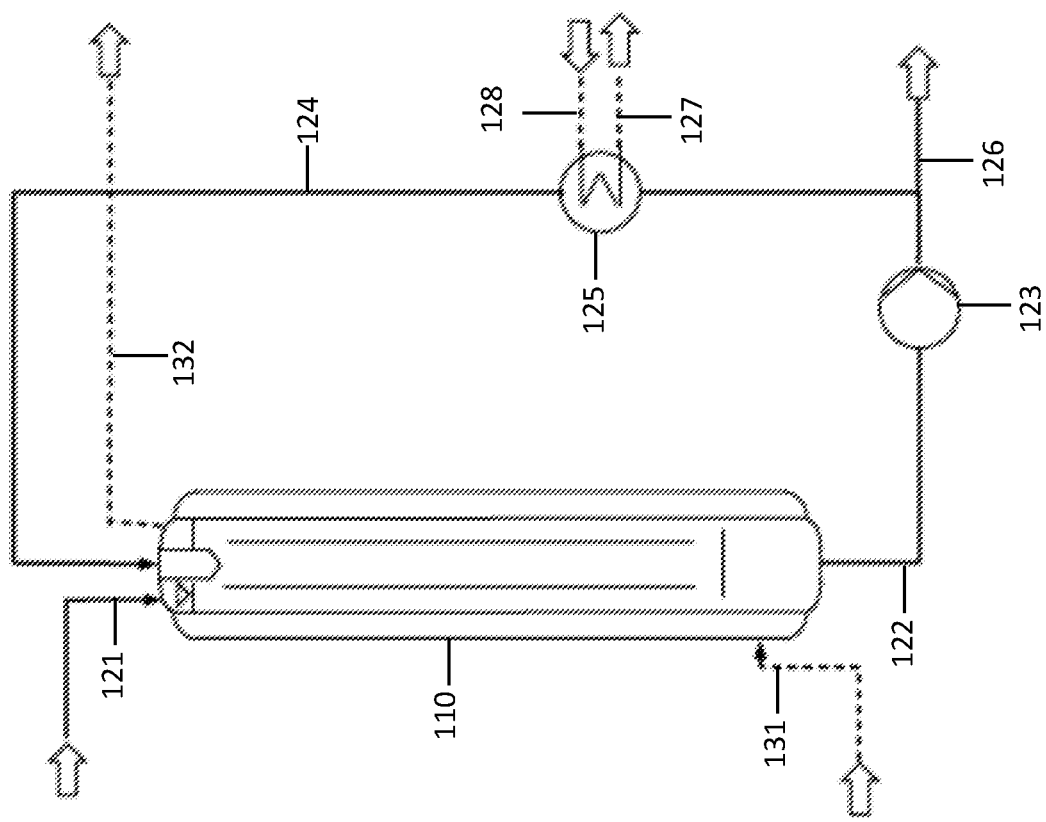
FIG. 1 shows a possible basic design of the reactor.

It is therefore the fundamental advantage underlying the process according to embodiments of the invention that the new catalytic process can be carried out at significantly lower temperatures of, for example, 150° C., and at much lower pressures of, for example, 50 bar.

The industrial process described here for the production of methanol represents a particularly economical and ecological conversion of CO and $H_2$ to methanol on the basis of a new catalytic approach with specific technical measures.

The first aspect of the specific industrial realisation is the implementation of the new catalytic approach substantially in a gas/liquid system, which differs from the previously known processes primarily in that the reaction is carried out in a liquid phase. Preferably, the catalysis can be carried out here as a homogeneous catalysis, wherein the catalyst is dissolved in a solvent, or immobilised catalysts are used, which convert the synthesis gas into methanol according to the new approach.

The advantage of the liquid phase, which contains homogeneous catalysts or immobilised catalysts, is that it can directly absorb and dissipate released heat so that, unlike in the conventional process, so-called hot spots do not occur, which can irreversibly change the catalyst due to local temperature increases and thus make it ineffective, and/or the higher local temperatures lead to unwanted side reactions and thus a loss of reactants without a gain in products. By using a liquid phase, the most intensive possible incorporation of the gaseous reactants $H_2$ and CO must be achieved. Most industrial gas-liquid reactors are based on stirred tanks with gas introduction (directly into the liquid or via the stirrer) or the bubble column reactor.

The bubble column reactor is the least costly form of gas-liquid reactor, which is why it is used most frequently. In addition to these typical gas-liquid reactors, there is also the loop reactor as a niche application. Typical loop reactors include jet zone loop reactors, impingement jet reactors, loop venturi reactors (buss loop reactors), jet loop reactors, and jet nozzle circulation reactors (jet loop reactors). This is used in particular in the form of the jet loop (jet loop reactor) in hydroformylation (homogeneous catalyst, CO+$H_2$+olefin→aldehyde) and in biocatalytic oxidations (enzyme, substrate+$O_2$→oxidised product). This type of reactor has been used up to now when the reaction rates are very fast, as is the case, for example, with hydroformylation and enzyme catalysis, so that the normal gas feed into the liquid in a bubble column reactor has a limiting effect and the reaction rate is thus determined by the material transport rate. Conversely, a bubble column reactor is usually used for slower reaction rates.

The second aspect is the performance of the gas-liquid reaction, in particular in a loop reactor, although this type of reactor is initially not obvious, since the reaction on which an embodiment of the invention is based with the previously known catalysts does not have such a fast reaction rate as hydroformylation or an enzyme catalysis. However, the methanol synthesis described herein is distinguished in that there is no metered addition of any additional substrates (other than $H_2$ and CO). This has the major disadvantage that the exothermic reaction does not continuously cool the reaction solution—unlike when other components are added. Therefore, the strongly exothermic reaction of the methanol synthesis leads to a strong heating over the course of the reaction. However, catalysts, especially homogeneous catalysts, have a specific temperature range in which they highly selectively catalyse the desired reaction. Methanol synthesis therefore requires intensive cooling.

The use of a loop reactor results in much better mixing of the gases with the liquid and distribution of the heat compared to the other gas-liquid reactors. Heat can be removed by internal or external heat exchangers. Internal heat exchangers are immersed directly in the reaction solution (e.g. cooling coils, U-tube, heat exchanger plates) or the reactor walls transfer the heat to heat exchangers. If the reaction solution is circulated in a circuit, the heat can also be dissipated via a heat exchanger in this external circuit. Although the catalytic systems described so far are not fast enough for loop reactors, the additional critical circumstance of heat removal due to the lack of continuous metered addition of co-substrates (except CO and $H_2$) makes this type of reactor particularly promising for industrial implementation.

The third aspect for the particularly economical implementation of this methanol synthesis is the use of one or more reactors and one or more external heat exchangers. Thus, depending on the size of the production plant, an optimum composition of the individual components can be selected.

The fourth aspect addresses the most economical separation of the methanol produced. This can be done in several successive steps based on the simple principle of phase separation. For example, not only a gas-liquid system can be used, but also the gas-liquid-liquid subgroup, which is distinguished by the presence of several liquid phases, exemplified by one phase being catalyst-rich and the other product-rich. By separating or continuously withdrawing the product-rich phase, the total flow quantity is reduced during the separation of the methanol. The methanol is then removed from the product-rich phase. This can be done by using methanol selective membranes (e.g. nanofiltration) or by a simple (flash evaporation) or multi-stage distillation (column).

In this process, the gaseous reactants hydrogen ($H_2$) and gaseous carbon monoxide (CO) are converted to methanol. The reaction takes place within a liquid. This liquid comprises at least one solvent, an alcohol and/or an amine as nucleophilic promoter and a catalyst. This catalyst can also be present in liquid form or as a solid in the liquid. The catalyst itself comprises at least one Lewis base ligand (e.g. N/N—H, O/O—H, S/S—H, C/C—H, Si/Si—H, B/B—H) and a transition metal. It is a metal catalyst with the basic structure M-LB, wherein M is a metal ion and LB is the centre of the at least one Lewis base. In its simplest form, the catalyst can be described as $M_xN_y$ (x=1-4, y=1-2), which is shown in Scheme 1:

Scheme 1

Simple examples would be manganese nitride or iron nitride. Besides artificial manganese nitride, natural minerals are also known, such as iron nitride like siderazote ($Fe_3N$) and roaldite ($Fe_4N$).

Furthermore, organometallic complexes as shown in Scheme 2 are well suited, wherein M is a metal ion and LB is the centre of the at least one Lewis base. In this variant, LB contains at least one atom selected from a group comprising N, P, O, S or C.

Scheme 2

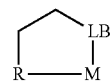

The transition metal is an ion selected from the group of manganese, rhenium, iron, ruthenium, chromium, molybdenum, tungsten, cobalt, rhodium, iridium, nickel or copper, palladium, platinum, wherein in particular manganese, iron, ruthenium or molybdenum have good properties. Above all, the use of manganese, ruthenium or molybdenum as central ion shows high conversion rates (TON).

Typical homogeneous catalysts include:

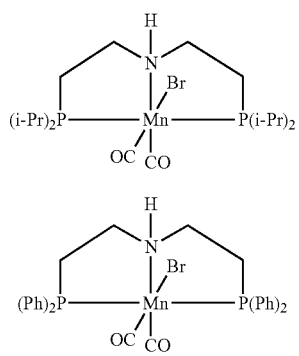

Mn-1

Mn-2

The reaction can also preferably take place in the presence of a base. In particular, it has been found that alcoholates can accelerate bases. Suitable bases include phosphates, sulphates, carbonates or alcoholates of lithium, sodium, potassium or calcium. For example, $K_3PO_4$ or KOMe has been used successfully.

This reaction can preferably take place in a bubble column, loop reactor, or jet loop reactor. Such reactor types are known from the continuous reaction of gases and at least one liquid. For example, WO 2010/923018 describes how compounds with olefinic double bonds are converted to aldehydes and/or alcohols using synthesis gas.

A loop reactor consists of a tubular reactor and a material recirculation system. This makes it possible to achieve reaction control with the properties between a tubular reactor and an ideally mixed stirred tank reactor. In the basic function, a gas mixture flows into the reactor, e.g. from above or below, so that a bubble column forms in the inner tube of the loop reactor. In addition to this actual tube reactor, there is a material recirculation system so that the reaction volume within the bubble reactor and the dwell time can be adjusted separately based on the proportion of the recirculated material flow. It is therefore crucial that in the loop reactor a spatial separation is made between upward flow direction and downward flow.

Loop reactors are therefore special bubble column reactors which, through the construction of a coaxial guide tube, directly impose a defined circulation on gas-laden rising liquid. There are several types of loop reactors. In the simplest case, gas is introduced into the guide tube through a central nozzle at the bottom of the reactor. The gas bubbles take the liquid upwards according to the principle of the airlift pump. The liquid flows back downwards under degassing via the upper edge between the reactor shell and the guide tube. Gas dispersion can be significantly improved by an additional propelling jet.

Two basic types of loop reactors can be distinguished, namely those with external loops where the spatial separation is clearly visible. Upflow and downflow columns are arranged as cylinders side by side and connected by a tube at the top and bottom. Loop reactors with internal loops have a smaller cylinder in the centre of a cylinder with larger diameter. The connection between the two cylinders is made possible by the smaller cylinder, which functions as a bubble reactor, being slightly shorter at both ends than the surrounding cylinder. This design is used especially for larger dimensions, as it is more space-saving.

A so-called jet loop reactor or jet nozzle reactor is distinguished by a homogeneous distribution of gas and liquid. In the jet loop reactor, the liquid is fed to the bottom of the reactor in a propelling jet in such a way that it can capture the gas and split the gas flow.

In an impingement jet reactor, at least two separate circulation flows are generated by several nozzles and are directed against each other. The arrangement results in a high specific power input in the impingement zone with a large material exchange capacity. The disadvantage is the more complex construction.

In the case of the so-called downflow loop reactor, the focus is on the fact that it is characterised by very large gas dwell times that can be set with a low overall height.

Loop reactors are used in many technical gas-liquid reactions. However, the focus here is on a liquid reactant reacting with a gaseous reactant. In the present case, however, a liquid reaction environment is provided by the solvent, in which the reaction product, which is also liquid, is then also found, wherein the two reactants hydrogen and carbon monoxide are present in gaseous form. Therefore, the use of loop reactors for the continuous reaction of gaseous reactants is not common.

Furthermore, in the present application, such a reactor preferably has at least one device for heat dissipation, since the reaction is highly exothermic.

It is thus possible to successfully produce methanol at much lower pressures and thus significantly lower CAPEX and OPEX costs.

Furthermore, it has proven to be advantageous to use at least two loops or jet loop reactors connected in parallel and/or in series, since the individual plant components can be dimensioned smaller in the case of a parallel connection, while a series connection has the advantage that the respective degrees of conversion can be controlled by the corresponding concentration of the catalyst and thus local temperature stresses due to the strongly exothermic reactions can be avoided.

With regard to the at least one device for heat dissipation, it has proven advantageous to provide this either directly inside the reactor or in the shell of the reactor in order to achieve the most homogeneous temperature control possible inside the reactor. In principle, however, it is also conceivable to design this device in such a way that a discharged product flow from the reactor is cooled. This simplifies the design.

In the same way, it is conceivable to integrate such a device for heat dissipation into the described circulation of the at least one reactor, i.e. the recirculation of the liquid, so that the liquid is cooled down again before coming into contact again with the reactants hydrogen and oxygen. Depending on the design of the loop reactor, this device for heat removal is then also found inside or outside the reactor shell.

Furthermore, it is also advantageous if the reactor is arranged as a jet loop bundle reactor, as this allows easy cooling between the individual reactors and thus enables parallel reaction control within the individual bubble columns within one apparatus. This also leads to a homogenisation of the temperature profile.

Alternatively or additionally, an embodiment of the invention also provides a process for the production of methanol from gaseous hydrogen and carbon monoxide, in which the hydrogen and the carbon monoxide are brought into contact with a liquid in at least one reactor. Said liquid comprises at least one solvent, an alcohol or an amine as a nucleophilic promoter and a catalyst. This catalyst comprises a transition metal and at least one Lewis base ligand. After the reaction has taken place, the methanol formed is present in the liquid phase which, after reaction, is transferred to a container in which a liquid phase and a gaseous phase are formed. This formation of the phase can be optionally supported by a pressure reduction of 5 to 90%, preferably 10 to 60% and particularly preferably 20 to 50% or to an absolute pressure between 1 and 20 bar, preferably 5 to 10 bar. As an optional supplement or alternative to lowering the pressure, the temperature can be lowered by cooling by at least 5%, preferably at least 20%, particularly preferably at least 50%.

The resulting product-rich phase contains the desired reaction product methanol in an amount of at least 55 wt. %, preferably at least 70 wt. %, and particularly preferably at least 90 wt. %, based on the total liquid phase which has been discharged from the reactor, while the solvent is present in the liquid phase in an amount of at least 55 wt. %, preferably at least 70 wt. %, and particularly preferably at least 90 wt. %. This allows a very easy separation of product and solvent.

It has turned out to be particularly favourable to recycle the liquid phase into at least one of the at least one reactors. Thus, on the one hand, the contained liquid with all its components, in particular the catalyst, is practically completely recycled, and, on the other hand, methanol contained therein is recycled again and can be separated again accordingly, so that there is also no loss of product as a result.

Furthermore, it has been found to be advantageous that an apparatus is connected downstream of the reactor and is arranged in such a way that the withdrawn liquid phase from the reactor first passes through this apparatus before entering the container. This apparatus can be used to segregate unreacted hydrogen and/or carbon monoxide from the liquid phase by simple phase separation. This can be favoured by slightly depressurising the system here, in particular reducing the pressure by 1 to 5 bar and/or lowering the temperature slightly, for example by 10 to 25° C., preferably 25 to 50° C. This enables the phase separation and at the same time a recirculation into the system is still possible.

In addition, it has proven to be advantageous that separated hydrogen and/or separated carbon monoxide from this apparatus is/are returned to at least one of the at least one reactors. In this way, the loss of reactant can be avoided and the overall efficiency of the process can be increased.

Irrespective of the choice of reactor and the type of purification, it has been found to be favourable if the alcohol and/or the amine as promoter in the liquid originates from a group comprising methanol, glycol, pyrrole, indole, aniline and derivatives of one of these aforementioned compounds.

Additionally or alternatively, it has also been found to be favourable if the alcohol and/or the amine is/are straight-chained as promoter, branched, or of cyclic structure. All embodiments lead to particularly high conversions.

Furthermore, it has proven to be favourable if the catalyst itself is only an indirect component of the liquid, i.e. it is not present in liquid form, but has been immobilised, i.e. bound to the surface of a solid body. This allows for easier catalyst exchange, for example. This solid body can be, for example, a sparingly soluble oxide, silicate, or polymer.

Conversely, a homogeneous catalyst offers the advantage that the reaction is practically completely independent of material transfer phenomena.

Furthermore, in the case of product separation by evaporation of the methanol, it has been found to be preferable if at least one solvent is used as an aliphatic solvent with a boiling point higher than methanol, since this allows for simple distillation-based separation of solvent residues in the methanol obtained.

In the case of product separation by means of membrane technology, nanofiltration is particularly suitable; in this case, care must be taken that all other components used differ significantly in molar mass from methanol. The catalyst, the promoter, the solvent and, if necessary, the base should be significantly larger and wider than methanol.

A further preferred embodiment provides for a reactor temperature between 20 and 180° C., preferably between 50 and 170° C., and particularly preferably between 80 and 150° C., since good conversions can be achieved at these reaction temperatures without damaging the catalyst. Pressures between 1 and 100 bar, preferably between 5 and 80 bar, particularly preferably between 10 and 50 bar, have proven to be favourable, whereby in any combination of the stated temperature and pressure ranges with each other, the overall load on the apparatus system can be significantly reduced compared to conventional heterogeneously catalysed methanol syntheses.

Lastly, the process can be carried out continuously or semi-continuously, which facilitates large-scale application. In particular, if the process is carried out continuously, the effluent of the liquid phase from the reactor and/or an inflow of hydrogen and/or carbon monoxide into the reactor can be used to control the process in an open-loop or closed-loop manner.

Further advantages and possible embodiments of the invention will also become apparent from the figures and the description thereof, with each feature being considered disclosed separately and in any combination.

FIG. 1 shows the basic design with use of a loop reactor. A heat exchange medium is introduced into the reactor 110 via line 131. The heat exchange medium is removed again via line 132.

This reactor contains a liquid in which a solvent, an alcohol and/or an amine, at least one nucleophilic promoter and a catalyst are found. Gas is also injected into the reactor 110 via line 121. This gas is a so-called synthesis gas mixture consisting of hydrogen and carbon monoxide.

A product flow is withdrawn from the reactor 110 via line 122 by means of the pump 123. Via line 126, parts of this flow are fed to a processing, while via line 124 the flow is returned to the reactor 110 after it has passed through the heat exchanger 125 and has thus cooled down. An apparatus for product separation can also be installed on the line 124. This can be, for example, a nanofiltration system in which the methanol can be continuously removed from the system. Upstream of the product separation apparatus, there can also be optionally a gas separation for unused carbon monoxide and hydrogen, so that gases not converted during methanol separation escape.

Figure 2:
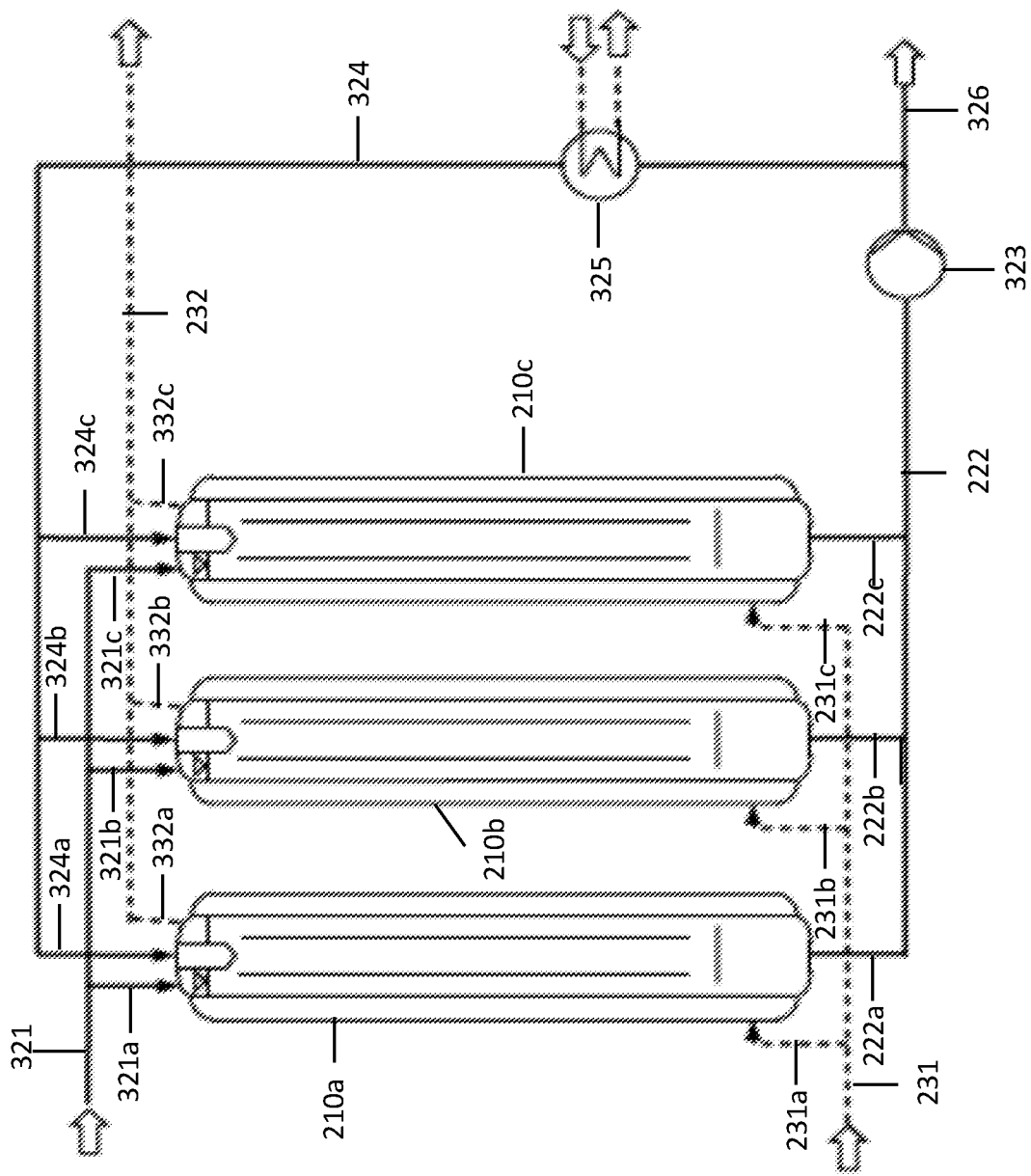
FIG. 2 shows a parallel connection of reactors.

FIG. 2 shows a possible parallel connection of three loop reactors 210*a*, 210*b* and 210*c*. Here, too, the heat exchange medium is fed via line 231 in each case, wherein the individual feed lines are named a, b, and c for the corresponding reactor. In the same way, the heat exchange medium is discharged again via the line 232 comprising the individual discharge lines 232*a*, 232*b* and 232*c*.

The required reaction gas of hydrogen and carbon monoxide is introduced into the reactors 210*a*, 210*b* and 210*c* via the line 221 comprising the inflow lines 221*a*, 221*b* and 221*c*. The product flow is removed via the line 222 and from the individual reactors 210*a*, 210*b* and 210*c* via lines 222*a*, 222*b* and 222*c* by means of pump 223. Individual parts of this flow are fed via line 226 to a processing. The remaining residual flow is cooled in the heat exchanger 225 and returned to the reactor via line 224 comprising the associated lines 224a, 224b, and 224c.

An apparatus for product separation can also be installed on line 324. This can be, for example, a nanofiltration system in which the methanol can be continuously removed from the system. Optionally, a gas separation for unused carbon monoxide and hydrogen can be installed upstream of the product separation apparatus so that gases not converted during methanol separation escape.

Figure 3:
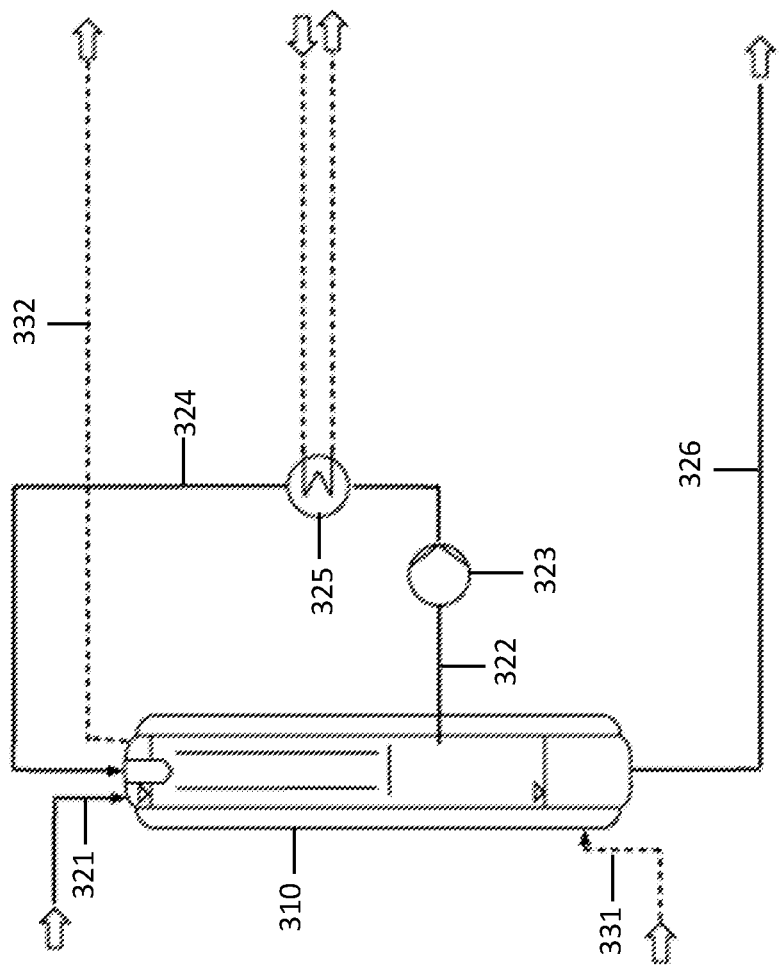
FIG. 3 shows another possible basic design of the reactor.

FIG. 3 shows the possibility of a separate removal of the recycled flow and the discharged flow. For this purpose, the gaseous reactants are fed in via line 321 and the portions removed from the circuit are discharged via line 326. The remaining part is pumped out via line 322 through the pump 323 and recirculated via the heat exchanger 325 into the associated line 324. Heat exchange medium enters the reactor 310 via the line 331 and is removed again via the line 332.

Figure 4:
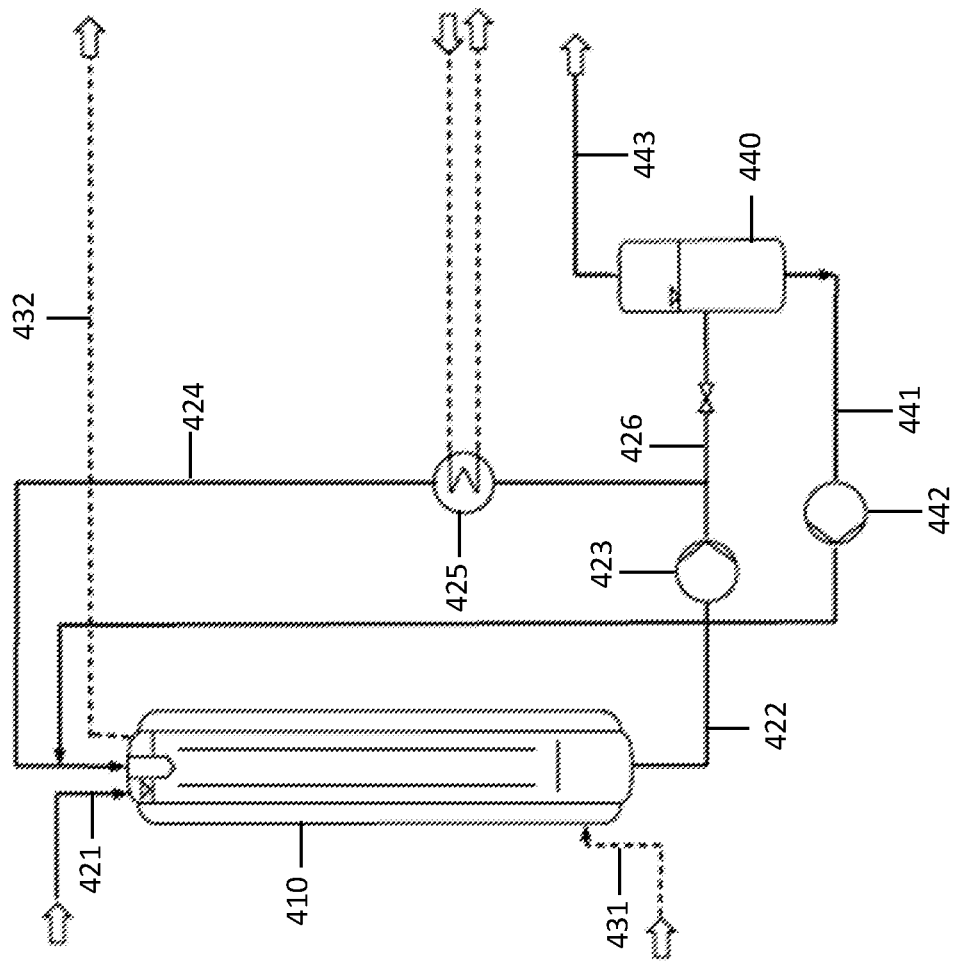
FIG. 4 shows a possible basic design of the reactor in combination with a single-stage processing.

FIG. 4 shows parts of an imaginary processing. It should be emphasised that, despite the illustration in combination with the loop reactor, this type of processing is also conceivable with any other type of reactor, just like the one shown in FIG. 5.

Heat exchange medium is introduced via line 421 and withdrawn again via line 432. Hydrogen and carbon monoxide are introduced in gaseous form via line 421 into the reactor 410 filled with the liquid according to an embodiment of the invention and withdrawn via line 422 by the pump 423. Parts of the flow thus withdrawn are fed back into the reactor 410 via line 424 and the associated heat exchanger 425.

The discharged partial flow 426 is fed to an apparatus 440. In this apparatus, a liquid and a gaseous phase are separated. This can be done by a pure phase separation. If necessary, this is conveyed by lowering the pressure of the system, for example by 10 to 80%, preferably 20 to 60%, preferably to an absolute value between 5 and 10 bar. A temperature reduction, preferably by 1 to 50%, is additionally or alternatively possible.

The gaseous phase, which contains the essential parts of the methanol fraction, is withdrawn via line 444. The liquid phase is fed back into the reactor 410 via line 441 by the pump 442, wherein the mixing can take place either in the form shown by mixing the flows from lines 421 and 441 or via separate introductions into the reactor. Cooling in the circulation line 441 is possible by at least one heat exchanger.

Figure 5:
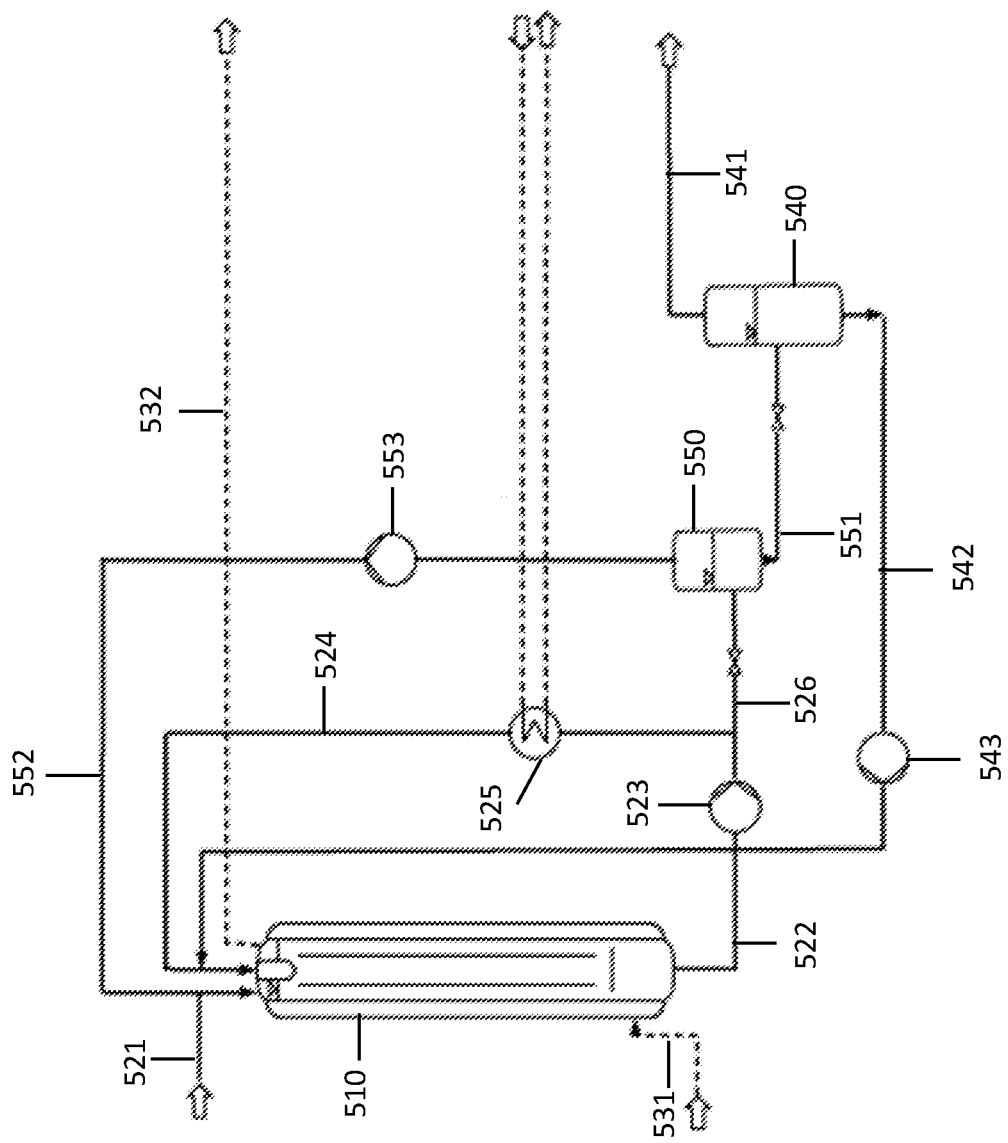
FIG. 5 shows a possible basic design of the reactor in combination with a two-stage processing.

Lastly, FIG. 5 shows an even more complex processing system, wherein the use of the loop reactor with its supply of the heat exchange medium via line 531 and the withdrawal of the heat exchange medium via line 532 is only optional.

Hydrogen and carbon monoxide are introduced as gaseous reactants into the reactor 510 via line 521 and withdrawn via line 522 by the pump 523. Partial recirculation back into the reactor 510 takes place via line 524 and the heat exchanger 525 arranged therein. Those parts of the flow from line 522 that are not circulated via line 524 are fed via line 526 into an apparatus 550. In this apparatus 550, a liquid phase and a gaseous phase are separated. This can be done by phase separation only. If necessary, this is conveyed by lowering the pressure of the system slightly, for example by 1 to 5%, preferably by up to 5 bar. A temperature reduction, preferably by 1 to 5%, is also conceivable additionally or alternatively.

The gaseous phase is returned to the reactor via line 552 by means of pump 553. The liquid phase obtained there is fed via line 551 to a further purification of the methanol contained there in a container 540. Here, the second phases are separated as described for FIG. 4.

From the container 540, the liquid phase is returned to the reactor 510 either directly or indirectly via line 542 through the pump 543. Further cooling is possible by means of a heat exchanger. The gaseous phase separated in the container 540 is fed via line 541 to a possible further methanol purification. This methanol purification can be a nanofiltration and/or a distillation.

Example

The 10 L Jet-loop reactor has a combined primary heating-cooling circuit and a secondary circuit designed exclusively for cooling.

2.48 g of a Mn(I)—PNP Catalyst (CAS 1919884-90-4)

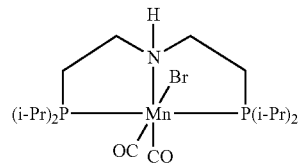

are added as well as 8.77 g of potassium methanolate (KOMe) as base, which was dissolved in 500 mL of 1-octanol at 50° C. This alcohol also functions as a promoter, alternatively methanol can be used. A total of 5.0 L of 1-octanol is used as solvent.

In a semi-continuous (semi-batch) operation, 104.5 NL/min of hydrogen and 49.8 NL/min of carbon monoxide were introduced at a pressure of 25 bar and an average temperature of 120° C. The main part of the reaction took place from about 110° C. and 25 bar within one hour. Under these experimental conditions, a turnover rate (TON) of 208 was determined in relation to the amount of catalyst used.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS

| | |
|---|---|
| 110 | reactor |
| 121, 122 | line |
| 123 | pump |
| 124 | line |
| 125 | heat exchanger |
| 126-128 | line |
| 131, 132 | line |
| 210a, 210b, 210c | reactor |
| 221, 122 | line |
| 223 | pump |
| 224 | line |
| 225 | heat exchanger |
| 226-228 | line |
| 231, 232 | line |
| 310 | reactor |
| 321, 322 | line |
| 323 | pump |
| 324 | line |
| 325 | heat exchanger |
| 326-328 | line |
| 410 | reactor |
| 421, 422 | line |
| 423 | pump |
| 424 | line |
| 425 | heat exchanger |
| 426, 428 | line |
| 431, 432 | line |
| 440 | phase separation apparatus |
| 441 | line |
| 442 | pump |
| 443 | line |
| 510 | reactor |
| 521, 522 | line |
| 523 | pump |
| 524 | line |
| 525 | heat exchanger |
| 526-528 | line |
| 531, 532 | line |
| 540 | phase separation apparatus |
| 541, 542 | line |
| 543 | pump |
| 543 | line |
| 550 | container |
| 551, 552 | line |
| 553 | pump |

The invention claimed is:

1. A process for the production of methanol from hydrogran and carbon monoxide, the process comprising:
contacting the hydrogen and carbon monoxide, which are both in gaseous form, with a liquid in at least one bubble or loop or jet loop reactor, wherein the liquid comprises at least one solvent, an alcohol and/or an amine as a nucleophilic promoter, optionally at least an additional base and a catalyst, the catalyst comprising a transition metal and at least one Lewis base ligand, wherein at least one device is provided for heat removal from the reactor, and wherein the methanol is formed as a product.

2. The process according to claim 1, wherein the at least one bubble or loop or jet loop reactor includes at least two bubble and/or loop and/or jet loop reactors connected in parallel and/or in series.

3. The process according to claim 1, wherein the at least one device for heat removal from the reactor is arranged inside the reactor or in a shall of the reactor.

4. The process according to claim 1, wherein the at least one device for heat removal from the reactor is integrated in a circuit of the at least one reactor.

5. The process according to claim 1, wherein the reactor is a loop-bundle reactor or jet-loop-bundle reactor.

6. A process for the production of methanol produced from hydrogen and carbon monoxide, the process comprising:
contacting the hydrogen and the carbon monoxide, which are both in gaseous form, with a liquid in at least one reactor, wherein the liquid contains at least one solvent, an alcohol or an amine as a nucleophilic promoter, optionally an additional base and a catalyst, wherein the catalyst comprises a transition metal and at least one Lewis base ligand, wherein the methanol formed is in a liquid phase, and wherein, after the reaction, the liquid phase is transferred to a container so that a liquid phase and a gaseous phase form, wherein the methanol formed is present in the gas-rich phase in an amount of at least 55 wt. % and traces of the solvent, catalyst, promoter, base are present in the liquid phase.

7. The process according to claim 6, wherein the methanol is produced according to a process for the production of methanol from hydrogen and carbon monoxide, the process comprising:
contacting the hydrogen and carbon monoxide with a liquid in at least one bubble or loop or jet loop reactor, wherein the liquid comprises at least one solvent, an alcohol and/or an amine as a nucleophilic promoter, optionally an additional base and a catalyst, the catalyst comprising a transition metal and at least one Lewis base ligand, wherein at least one device is provided for heat removal from the reactor, and wherein the methanol is formed as a product.

8. The process according to claim 6, wherein the liquid phase is recycled from the container to the at least one reactor.

9. The process according to claim 6, wherein a segregation between unreacted hydrogen and carbon monoxide and the liquid phase takes place in an apparatus downstream of the reactor and before entry into the container.

10. The process according to claim 9, wherein hydrogen and/or carbon monoxide are recycled from the apparatus to the at least one reactor.

11. The process according to claim 1, wherein, as the alcohol and/or the amine as the nucleophilic promoter, at least one compound is selected from a group comprising methanol, glycol, pyrrole, indole, aniline and derivatives of one of the compounds of this group.

12. The process according to claim 1, wherein the alcohol and/or the amines as the nucleophilic promoter is/are straight-chained, branched or of cyclic structure.

13. The process according to claim 1, wherein the catalyst is present bound to the surface of a solid body.

14. The process according to claim 1, wherein the at least one solvent is an aliphatic solvent having a boiling point higher than methanol.

15. The process according to claim 1, wherein a temperature of between 20 and 180° C. is present in the at least one reactor, and wherein a pressure of 1 to 100 bar is present in the at least one reactor.

16. The process according to claim 1, wherein the process is carried out continuously or semi-continuously.

17. The process according to claim 1, wherein the process is carried out continuously, and wherein an outflow of the liquid phase from the reactor and/or an inflow of hydrogen and/or carbon monoxide into the reactor is used to control the process in an open-loop or closed-loop manner.

\* \* \* \* \*